US012776409B2

(12) United States Patent

Srour et al.

(10) Patent No.: US 12,776,409 B2

(45) Date of Patent: Oct. 27, 2026

(54) EAR-WEARABLE DEVICE SYSTEMS AND METHODS FOR MONITORING EMOTIONAL STATE

(71) Applicant: Starkey Laboratories, Inc., Eden Prairie, MN (US)

(72) Inventors: Majd Srour, Nesher (IL); Amit Shahar, Hod HaSharon (IL); Roy Talman, Herzliya (IL)

(73) Assignee: Starkey Laboratories, Inc., Eden Prairie, MN (US)

( * ) Notice: Subject to any disclaimer, the term of this patent is extended or adjusted under 35 U.S.C. 154(b) by 141 days.

(21) Appl. No.: 17/526,416

(22) Filed: Nov. 15, 2021

(65) Prior Publication Data

US 2022/0157434 A1 May 19, 2022

Related U.S. Application Data

(60) Provisional application No. 63/114,284, filed on Nov. 16, 2020.

(51) Int. Cl.

*G16H 20/70* (2018.01)
*A61B 5/00* (2006.01)
*A61B 5/16* (2006.01)

(52) U.S. Cl.

CPC ............. *G16H 20/70* (2018.01); *A61B 5/165* (2013.01); *A61B 5/4803* (2013.01); *A61B 5/6815* (2013.01); *A61B 5/741* (2013.01)

(58) Field of Classification Search

CPC ...... G16H 20/70; A61B 5/165; A61B 5/4803; A61B 5/6815; A61B 5/741

See application file for complete search history.

(56) References Cited

U.S. PATENT DOCUMENTS 4,093,821 A * 6/1978 Williamson ............ G10L 25/90 704/207
6,283,915 B1 9/2001 Aceti et al.

(Continued)

FOREIGN PATENT DOCUMENTS

CN 109498036 3/2019
CN 111407255 A * 7/2020

(Continued)

OTHER PUBLICATIONS

Fletcher et al., "Wearable Sensors: Opportunities and Challenges for Low-Cost Health Care," 32nd Annual International Conference of the IEEE EMBS Buenos Aires, Argentina, Aug. 31-Sep. 4, 2010. (Year: 2010).*

(Continued)

*Primary Examiner* — Jonathon A. Szumny

(74) *Attorney, Agent, or Firm* — Pauly, DeVries Smith & Deffner LLC

(57) ABSTRACT

Embodiments herein relate to ear-wearable device systems and methods for monitoring a device wearer's emotional state and status. In an embodiment, an ear-wearable device is included having a control circuit, a microphone, and a power supply circuit. The ear-wearable device is configured to monitor signals from the microphone, identify signs of anxiety in the microphone signals, and provide a wearer of the ear-wearable device with feedback related to identified anxiety. In another embodiment, a method of monitoring anxiety with an ear-wearable device is included, the method including monitoring signals from a microphone, identifying signs of anxiety in the microphone signals, and providing a wearer of the ear-wearable device with feedback related to the identified anxiety. Other embodiments are also included herein.

16 Claims, 11 Drawing Sheets

(56) References Cited

U.S. PATENT DOCUMENTS

| | | | |
|---|---|---|---|
| 6,638,217 | B1 | 10/2003 | Liberman |
| 7,165,033 | B1 | 1/2007 | Liberman |
| 7,340,393 | B2 * | 3/2008 | Mitsuyoshi ........... G10L 13/033 704/200 |
| 8,194,899 | B2 | 6/2012 | Naylor |
| 8,326,635 | B2 * | 12/2012 | Usher ...................... H04R 1/10 704/274 |
| 8,923,543 | B2 | 12/2014 | Sacha et al. |
| 9,167,356 | B2 | 10/2015 | Higgins et al. |
| 9,210,518 | B2 | 12/2015 | Zhang |
| 9,219,964 | B2 | 12/2015 | Merks |
| 9,501,765 | B2 | 11/2016 | Grigg et al. |
| 9,510,765 | B2 | 12/2016 | Greder |
| 9,848,273 | B1 | 12/2017 | Helwani et al. |
| 9,924,271 | B2 | 3/2018 | Lai et al. |
| 10,204,642 | B2 | 2/2019 | Levanon |
| 10,242,501 | B1 * | 3/2019 | Pusch .................... H04N 19/43 |
| 10,537,268 | B2 | 1/2020 | Micheyl et al. |
| 10,595,730 | B2 | 3/2020 | Leboeuf et al. |
| 10,617,842 | B2 | 4/2020 | Espi Maques et al. |
| 10,893,835 | B2 | 1/2021 | Leboeuf et al. |
| 11,483,513 | B1 * | 10/2022 | Waggoner ................ H04N 5/60 |
| 12,446,778 | B2 | 10/2025 | Srour et al. |
| 2001/0016048 | A1 * | 8/2001 | Rapeli ...................... H03G 3/32 381/104 |
| 2003/0012253 | A1 * | 1/2003 | Pavlidis ................. A61B 5/164 374/45 |
| 2006/0116311 | A1 | 6/2006 | Baum et al. |
| 2008/0038706 | A1 | 2/2008 | Dameshek |
| 2009/0005657 | A1 | 1/2009 | Bodlaender et al. |
| 2009/0234586 | A1 * | 9/2009 | Tanaka ............... G01N 33/6812 702/179 |
| 2009/0264711 | A1 * | 10/2009 | Schuler .................. A61B 5/165 600/300 |
| 2010/0280336 | A1 * | 11/2010 | Giftakis ............... A61B 5/4803 600/301 |
| 2012/0015045 | A1 | 1/2012 | Krishna et al. |
| 2012/0150545 | A1 | 6/2012 | Simon |
| 2013/0013208 | A1 * | 1/2013 | Ohnemus ............... G16H 50/30 702/19 |
| 2013/0060150 | A1 * | 3/2013 | Song ...................... A61B 7/003 600/529 |
| 2013/0195302 | A1 * | 8/2013 | Meincke .............. H04R 25/356 381/321 |
| 2013/0225950 | A1 * | 8/2013 | Van Elswijk .......... G16H 10/20 600/309 |
| 2013/0274586 | A1 * | 10/2013 | Miyazaki ............... A61B 5/165 600/407 |
| 2013/0343584 | A1 | 12/2013 | Bennett et al. |
| 2014/0111690 | A1 * | 4/2014 | Kim ................. H04N 21/42201 348/565 |
| 2014/0206945 | A1 * | 7/2014 | Liao ....................... G16H 50/20 607/45 |
| 2014/0351133 | A1 | 11/2014 | Christian et al. |
| 2015/0099946 | A1 * | 4/2015 | Sahin ....................... A61B 7/04 600/301 |
| 2015/0223731 | A1 * | 8/2015 | Sahin ....................... A61B 5/16 600/595 |
| 2015/0297109 | A1 | 10/2015 | Garten et al. |
| 2015/0331941 | A1 * | 11/2015 | Defouw ............... H04N 21/233 707/687 |
| 2015/0350201 | A1 * | 12/2015 | Cornell ............... G06F 16/9535 726/7 |
| 2017/0020442 | A1 | 1/2017 | Flitsch et al. |
| 2017/0127993 | A1 | 5/2017 | Olivier et al. |
| 2017/0143246 | A1 * | 5/2017 | Flickinger ............ A61B 5/6898 |
| 2017/0220772 | A1 * | 8/2017 | Vleugels ................ G16H 50/70 |
| 2017/0221336 | A1 | 8/2017 | Ogaz |
| 2017/0339484 | A1 * | 11/2017 | Kim ....................... A61B 5/165 |
| 2017/0347177 | A1 | 11/2017 | Masaki et al. |
| 2018/0032682 | A1 * | 2/2018 | Donalds ................. G16H 30/20 |
| 2018/0061411 | A1 | 3/2018 | Bhat |
| 2018/0107943 | A1 * | 4/2018 | White ...................... G06N 5/01 |
| 2018/0133507 | A1 | 5/2018 | Malchano et al. |
| 2018/0242860 | A1 | 8/2018 | Leboeuf et al. |
| 2018/0268821 | A1 | 9/2018 | Levanon |
| 2018/0288813 | A1 * | 10/2018 | Asnis ...................... H04L 41/08 |
| 2018/0296092 | A1 * | 10/2018 | Hassan .................. G16H 50/20 |
| 2018/0317837 | A1 | 11/2018 | Burwinkel et al. |
| 2019/0132683 | A1 | 5/2019 | Sacha et al. |
| 2019/0206424 | A1 | 7/2019 | Feast et al. |
| 2019/0307388 | A1 * | 10/2019 | Bobo .................. A61B 5/7282 |
| 2019/0336724 | A1 * | 11/2019 | Li .......................... A61B 5/165 |
| 2019/0350524 | A1 * | 11/2019 | Hurley .................. A61B 5/486 |
| 2020/0008708 | A1 | 1/2020 | Tan et al. |
| 2020/0075039 | A1 * | 3/2020 | Eleftheriou ............ G06V 40/20 |
| 2020/0143703 | A1 | 5/2020 | Fabry et al. |
| 2020/0176018 | A1 * | 6/2020 | Feinauer ................ G10L 25/63 |
| 2020/0196977 | A1 | 6/2020 | Martin et al. |
| 2020/0245938 | A1 | 8/2020 | Xu et al. |
| 2020/0268265 | A1 | 8/2020 | Walsh et al. |
| 2020/0268315 | A1 | 8/2020 | Burwinkel et al. |
| 2021/0068736 | A1 | 3/2021 | Grahm et al. |
| 2021/0103426 | A1 | 4/2021 | Heo |
| 2021/0146082 | A1 * | 5/2021 | Härmä .................. G16H 20/40 |
| 2021/0169425 | A1 * | 6/2021 | Dirkes ................. A61B 5/7221 |
| 2021/0174805 | A1 * | 6/2021 | Wang ...................... G10L 25/63 |
| 2021/0191506 | A1 * | 6/2021 | Wang ...................... G06F 3/017 |
| 2021/0306771 | A1 * | 9/2021 | El Guindi .............. A61B 5/053 |
| 2021/0353903 | A1 * | 11/2021 | Park ....................... A61B 5/486 |
| 2022/0059122 | A1 * | 2/2022 | Xiu ......................... G10L 17/04 |
| 2022/0095973 | A1 * | 3/2022 | Luciani .................. G16H 10/60 |
| 2022/0108624 | A1 * | 4/2022 | Kwatra .................. G06V 20/41 |
| 2022/0167916 | A1 | 6/2022 | Mohanty et al. |
| 2022/0225034 | A1 | 7/2022 | Burns |
| 2022/0272465 | A1 * | 8/2022 | Boldt ..................... A61B 5/165 |
| 2022/0344030 | A1 * | 10/2022 | Abbas .................... G16H 50/20 |
| 2023/0016667 | A1 | 1/2023 | Srour et al. |
| 2023/0104641 | A1 * | 4/2023 | Garcia i Tormo ....... A61B 5/01 |
| 2023/0181869 | A1 | 6/2023 | Reinhart et al. |
| 2023/0240595 | A1 * | 8/2023 | Tiron ..................... G16H 10/60 600/301 |
| 2023/0301580 | A1 | 9/2023 | Xiao et al. |
| 2023/0372662 | A1 * | 11/2023 | Ratmansky ........... A61M 21/00 |
| 2024/0090808 | A1 | 3/2024 | Bhowmik et al. |
| 2025/0006354 | A1 * | 1/2025 | Larcher .................. G16H 10/20 |

FOREIGN PATENT DOCUMENTS

| | | | |
|---|---|---|---|
| DE | 102009043775 | 4/2011 | |
| JP | 2019533505 A * | 11/2019 | ........... A61B 5/0205 |
| KR | 101979297 | 8/2019 | |
| WO | 2018205013 | 11/2018 | |
| WO | 2019209986 | 10/2019 | |
| WO | 2020176533 | 9/2020 | |
| WO | 2020236911 | 11/2020 | |
| WO | WO-2020257352 A1 * | 12/2020 | ............ G16H 20/70 |
| WO | 2021127228 | 6/2021 | |
| WO | 2022026557 | 2/2022 | |
| WO | 2022170091 | 8/2022 | |

OTHER PUBLICATIONS

Epstein et al., "Why your sleep and wake cycles affect your mood," Harvard Health Publishing, https://www.health.harvard.edu/blog/why-your-sleep-and-wake-cycles-affect-your-mood-2020051319792. (Year: 2020).*

Athavipach et al., "A Wearable In-Ear EEG Device for Emotion Monitoring," Sensors 2019, 19, 4014; doi: 10.3390/s19184014. (Year 2019).*

"International Search Report and Written Opinion," for PCT Application No. PCT/US2020/065686 mailed Mar. 29, 2021 (14 pages).

Savov, Vlad "Amazon Preparing a Wearable That 'Reads Human Emotions,' says report," The Verge, May 23, 2019. https://www.theverge.com/circuitbreaker/2019/5/23/18636839/amazon-wearable-emotions-report (3 pages).

"Classic Tac Kit," Neuro Tek EMDR Product details available at URL <https://neurotekcorp.com/classic-tac-kit/> at least as early as Jul. 4, 2022 (4 pages).

(56) References Cited

OTHER PUBLICATIONS

"International Preliminary Report and Written Opinion," for PCT Application No. PCT/US2020/065686 mailed Jun. 30, 2022 (9 pages).
"International Preliminary Report on Patentability," for PCT Application No. PCT/US2022/015304 mailed Aug. 17, 2023 (20 pages).
"International Search Report and Written Opinion," for PCT Application No. PCT/US2022/015304 mailed Jul. 15, 2022 (27 pages).
"Invitation to Pay Additional Fees," for PCT Application No. PCT/US2022/015304 mailed May 4, 2022 (23 pages).
"Post-traumatic Stress Disorder (PTSD)," Mayo Clinic Overview, Symptoms, and Causes available at URL <https://www.mayoclinic.org/diseases-conditions/post-traumatic-stress-disorder/symptoms-causes/syc-20355967> at least as early as Oct. 9, 2017 (5 pages).
"Post-Traumatic Stress Disorder," MedlinePlus National Institutes of Health/National Library of Medicine PTSD information available at URL <https://medlineplus.gov/posttraumaticstressdisorder.htmll> at least as early as Jul. 27, 2016 (7 pages).
Bobade, Pramod, et al. "Stress Detection with Machine Learning and Deep Learning using Multimodal Physiological Data," Proceedings of the Second International Conference on Inventive Research in Computing Application (ICIRCA-2020) IEEE Xplore Part No. CFP20N67-ART (7 pages).
Brod, Samuel, et al. "As above, so below' examining the interplay between emotion and the immune system," Immunology (2014) 143, 311-318 (8 pages).
Can, Yekta Said, et al. "Continuous Stress Detection Using Wearable Sensors in Real Life: Algorithmic Programming Contest Case Study," Sensors 2019, 19, 1849 (21 pages).
Gunter, Raymond W, et al. "How eye movements affect unpleasant memories: Support for a working-memory account," Behaviour Research and Therapy 46 (2008) 913-931 (19 pages).
Healy, Eric W, et al. "An algorithm to improve speech recognition in noise for hearing-impaired listeners," J. Acoust. Sco. Am. 134 (4), Oct. 2013 pp. 3029-3038 (10 pages).
Jiang, Wei, et al. "Speech Emotion Recognition with Heterogeneous Feature Unification of Deep Neural Network," Sensors 2019, 19 2730 (15 pages).
Kyriakou, Kalliopi, et al. "Detecting Moments of Stress from Measurements of Wearable Physiological Sensors," Sensors 2019, 19, 3805 (26 pages).
Lee, Christopher William, et al. "A meta-analysis of the contribution of eye movements in processing emotional memories," J. Behav. Ther. & Exp. Psychiat. 44 (2013) 231-239 (9 pages).
Mackenzie, Ruairi J" Can we Really Measure Stress?," Technology Networks Neuroscience Article published Jun. 13, 2019. Available at URL <https://www.technologynetworks.com/neuroscience/articles/can-we-really-measure-stress-320611> (7 pages).
Mayo Clinic Staff "Stress symptoms: Effects on your body and behavior—Stress Management," Mayo Clinic Healthy Lifestyle article Published Mar. 24, 2021 at URL <https://www.mayoclinic.org/healthy-lifestyle/stress-management/in-depth/stress-symptoms/art-20050987?p=1> (2 pages).
Rachakonda, Laavanya, et al."iLog: An Intelligent Device for Automated Food Intake Monitoring and Stress Detection in the IoMT," IEEE Transactions on Consumer Electronics, IEEE Service Center, vol. 66 No. 2, Feb. 25, 2020 (10 pages).
Rachakonda, Laavanya, et al."Stress-Log: An IoT-based Smart System to Monitor Stress-Eating," 2019 IEEE International Conference on Consumer Electronics (ICCE), IEEE, Jan. 11, 2019 (6 pages).
Schubert, Sarah J, et al. "The efficacy and psychophysiological correlates of dual- attention tasks in eye movement desensitization and reprocessing (EMDR)," Journal of Anxiety Disorders 25 (2011) 1-11 (11 pages).
Seoane, Fernando, et al. "Wearable Biomedical Measurement Systems for Assessment of Mental Stress of Combatants in Real Time," Sensors 2014, 14, 7120-7141 (22 pages).
Yaribeygi, Habib, et al. "The Impact of Stress on Body Function: A Review," EXCLI Journal 2017; 16: 1057-1072 (16 pages).
Zamkah, Abdulaziz, et al. "Identification of Suitable Biomarkers for Stress and Emotion Detection for Future personal Affective Wearable Sensors," Biosensors 2020, 10, 40 (15 pages).
"Examination Report," for European Patent Application No. 20842767.4 mailed Feb. 6, 2024 (5 pages).
"Non-Final Office Action," for U.S. Appl. No. 17/786,673 mailed Apr. 2, 2024 (25 pages).
"Response to Non-Final Office Action," for U.S. Appl. No. 17/786,673 filed Jun. 19, 2024 (10 pages).
"Final Office Action," for U.S. Appl. No. 17/786,673 mailed Aug. 30, 2024 (23 pages).
"Non-Final Office Action," for U.S. Appl. No. 17/786,673 mailed Jan. 24, 2025 (23 pages).
"Response to Final Office Action," for U.S. Appl. No. 17/786,673 filed Dec. 30, 2024 (12 pages).
"Response to Final Office Action," for U.S. Appl. No. 17/786,673 filed Nov. 25, 2024 (11 pages).
"Response to Non-Final Office Action," for U.S. Appl. No. 17/786,673, filed on Apr. 22, 2022 (12 pages).
"Examination Report," for European Patent Application No. 20842767.4 mailed Aug. 26, 2026 (5 pages).
"Notice of Allowance," for U.S. Appl. No. 17/786,673 mailed Jun. 23, 2025 (8 pages).
"Non-Final Office Action," for U.S. Appl. No. 18/062,402 mailed Dec. 9, 2025 (37 pages).
"Reply to Communication per Article 94(3)," for EP Application No. 20842767.4, mailed Aug. 26, 2025 (10 pages).
"Non-Final Office Action," for U.S. Appl. No. 18/275,861 mailed Oct. 31, 2025 (41 pages).
"Response to Non-Final Office Action," for U.S. Appl. No. 18/062,402, filed on Mar. 9, 2026 (13 pages).
"Response to Non-Final Office Action," for U.S. Appl. No. 18/275,861, filed on Feb. 2, 2026 (10 pages).
"Communication pursuant to Article 94(3) EPC," for European Patent Application No. 20842767.4 mailed Apr. 23, 2025 (25 pages).
"Final Office Action," for U.S. Appl. No. 18/062,402 mailed Apr. 28, 2026 (19 pages).
"Final Office Action," for U.S. Appl. No. 18/275,861 mailed May 7, 2026 (20 pages).

* cited by examiner

EAR-WEARABLE DEVICE SYSTEMS AND METHODS FOR MONITORING EMOTIONAL STATE

This application claims the benefit of U.S. Provisional Application No. 63/114,284, filed Nov. 16, 2020, the content of which is herein incorporated by reference in its entirety.

FIELD

Embodiments herein relate to ear-wearable device systems and methods. More specifically, embodiments herein relate to ear-wearable device systems and methods for monitoring a device wearer's emotional state and status.

BACKGROUND

Mental state, both short term and long term, is a key factor in fully understanding a patient's health status. Emotions such as sadness, anger, and anxiety can have a direct adverse impact on health. Significant long-term stress is also well known to have an adverse impact on health.

Stress inducing events trigger the fight or flight response and prompt the adrenal glands to release hormones, including adrenaline and cortisol. Adrenaline functions to increase heart rate, elevate blood pressure and boost energy supplies. Cortisol, the primary stress hormone, functions to increase glucose levels in the bloodstream, enhance the brain's use of glucose and increase the availability of substances that repair tissues. Cortisol also curbs functions that would be nonessential or detrimental in a fight-or-flight situation. It alters immune system responses and suppresses the digestive system, the reproductive system and growth processes. The systems involved in a stress response also communicate with the brain regions that control mood, motivation and fear. Emotions, particularly negative ones, can be more intense when coupled with a stress response.

Usually, the body's stress-response system is self-limiting. Once a perceived threat has passed, hormone levels return to normal. As adrenaline and cortisol levels drop, heart rate and blood pressure return to baseline levels, and other systems resume their regular activities. However, the long-term activation of the stress-response system and the overexposure to cortisol and other stress hormones that follows can disrupt many normal processes of the body resulting in an increased risk of many health problems, including: anxiety, depression, digestive problems, headaches, heart disease, sleep problems, weight gain, and memory and concentration impairment.

SUMMARY

Embodiments herein relate to ear-wearable device systems and methods for monitoring a device wearer's emotional state and status. In a first aspect, an ear-wearable device is included having a control circuit, a microphone, and a power supply circuit. The ear-wearable device is configured to monitor signals from the microphone, identify signs of anxiety in the microphone signals, and provide a wearer of the ear-wearable device with feedback related to identified anxiety.

In a second aspect, in addition to one or more of the preceding or following aspects, or in the alternative to some aspects, the feedback includes suggested anxiety interventions.

In a third aspect, in addition to one or more of the preceding or following aspects, or in the alternative to some aspects, the anxiety interventions include breathing instructions.

In a fourth aspect, in addition to one or more of the preceding or following aspects, or in the alternative to some aspects, the feedback includes auditory feedback that indicates that anxiety was identified and provides suggested anxiety interventions.

In a fifth aspect, in addition to one or more of the preceding or following aspects, or in the alternative to some aspects, the ear-wearable device can further include a sensor package, the sensor package can include at least one selected from the group consisting of a motion sensor, a heart rate sensor, a temperature sensor, a respiratory rate sensor, and an SpO2 sensor, wherein the ear-wearable device is configured to monitor signals from the sensor package to identify signs of anxiety.

In a sixth aspect, in addition to one or more of the preceding or following aspects, or in the alternative to some aspects, signs of anxiety include a change in microphone signals along with a change in signals from at least one sensor in the sensor package.

In a seventh aspect, in addition to one or more of the preceding or following aspects, or in the alternative to some aspects, signs of anxiety include at least one of tonal change, volume change, and change of vocal cadence.

In an eighth aspect, in addition to one or more of the preceding or following aspects, or in the alternative to some aspects, the ear-wearable device is configured to analyze signals from the microphone in order to identify speech of a wearer of the ear-wearable device.

In a ninth aspect, in addition to one or more of the preceding or following aspects, or in the alternative to some aspects, the signs of anxiety include a change in the speech of the wearer of the ear-wearable device.

In a tenth aspect, in addition to one or more of the preceding or following aspects, or in the alternative to some aspects, the ear-wearable device is configured to determine a baseline value of anxiety for a wearer of the ear-wearable device.

In an eleventh aspect, in addition to one or more of the preceding or following aspects, or in the alternative to some aspects, the baseline value accounts for at least one of language, culture, and persona of the wearer of the ear-wearable device.

In a twelfth aspect, in addition to one or more of the preceding or following aspects, or in the alternative to some aspects, the ear-wearable device is configured to transmit data based on microphone signals to a separate device.

In a thirteenth aspect, in addition to one or more of the preceding or following aspects, or in the alternative to some aspects, the separate device includes an external accessory device.

In a fourteenth aspect, a method of monitoring anxiety with an ear-wearable device is included, the method including monitoring signals from a microphone, identifying signs of anxiety in the microphone signals, and providing a wearer of the ear-wearable device with feedback related to the identified anxiety.

In a fifteenth aspect, in addition to one or more of the preceding or following aspects, or in the alternative to some aspects, the feedback includes suggested anxiety interventions.

In a sixteenth aspect, in addition to one or more of the preceding or following aspects, or in the alternative to some aspects, the anxiety interventions including breathing instructions.

In a seventeenth aspect, in addition to one or more of the preceding or following aspects, or in the alternative to some aspects, the feedback includes auditory feedback that indicates that anxiety was identified and provides suggested anxiety interventions.

In an eighteenth aspect, in addition to one or more of the preceding or following aspects, or in the alternative to some aspects, the method can further include monitoring signals from a sensor package to identify signs of anxiety, wherein the sensor package includes at least one selected from the group consisting of a motion sensor, a heart rate sensor, a temperature sensor, a respiratory rate sensor, and an SpO2 sensor.

In a nineteenth aspect, in addition to one or more of the preceding or following aspects, or in the alternative to some aspects, signs of anxiety can include a change in microphone signals along with a change in signals from at least one sensor in the sensor package.

In a twentieth aspect, in addition to one or more of the preceding or following aspects, or in the alternative to some aspects, signs of anxiety can include at least one of tonal change, volume change, and change of vocal cadence.

In a twenty-first aspect, in addition to one or more of the preceding or following aspects, or in the alternative to some aspects, the method can further include analyzing signals from the microphone in order to identify speech of a wearer of the ear-wearable device.

In a twenty-second aspect, in addition to one or more of the preceding or following aspects, or in the alternative to some aspects, signs of anxiety can include a change in the speech of the wearer of the ear-wearable device.

In a twenty-third aspect, in addition to one or more of the preceding or following aspects, or in the alternative to some aspects, the ear-wearable device is configured to determine a baseline value of anxiety for a wearer of the ear-wearable device.

In a twenty-fourth aspect, in addition to one or more of the preceding or following aspects, or in the alternative to some aspects, the baseline value accounts for at least one of language, culture, and persona of the wearer of the ear-wearable device.

In a twenty-fifth aspect, in addition to one or more of the preceding or following aspects, or in the alternative to some aspects, the method can further include transmitting data based on microphone signals to a separate device.

In a twenty-sixth aspect, in addition to one or more of the preceding or following aspects, or in the alternative to some aspects, the separate device can include an external accessory device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, mental condition is a key factor in determining and understanding patient health. Negative emotions and stress can be very detrimental to an individual's health over time. Thus, understanding an individual's emotional state and status can allow for systems and/or health care providers to provide recommendations to help promote behavioral changes for healthier habits that can bring patients to live healthier and happier lives. Further, monitoring an individual's emotional state and status over time can help detect deteriorating mental conditions which could be an early indication of depression or other mental conditions.

Embodiments herein can include systems and devices configured to perform speech-based emotion monitoring to detect anxiety, including PTSD. Systems and devices herein can utilize microphones and vocal biomarkers to passively monitor patient emotions. When signs of anxiety are detected, auditory feedback can be provided to the individual that identifies the emotion followed by suggested interventions. This self-awareness/self-care intervention can be effective in reducing unnecessary emergency room/clinic visits for somatic symptoms (chest pain, rapid heart rate) related to anxiety.

In an embodiment, an ear-wearable device is included having a control circuit, a microphone, and a power supply circuit. The ear-wearable device is configured to monitor signals from the microphone, identify signs of anxiety in the microphone signals, and provide a wearer of the ear-wearable device with feedback related to identified anxiety.

In another embodiment, a method of monitoring anxiety with an ear-wearable device is included, the method including monitoring signals from a microphone, identifying signs of anxiety in the microphone signals, and providing a wearer of the ear-wearable device with feedback related to the identified anxiety.

Figure 1:
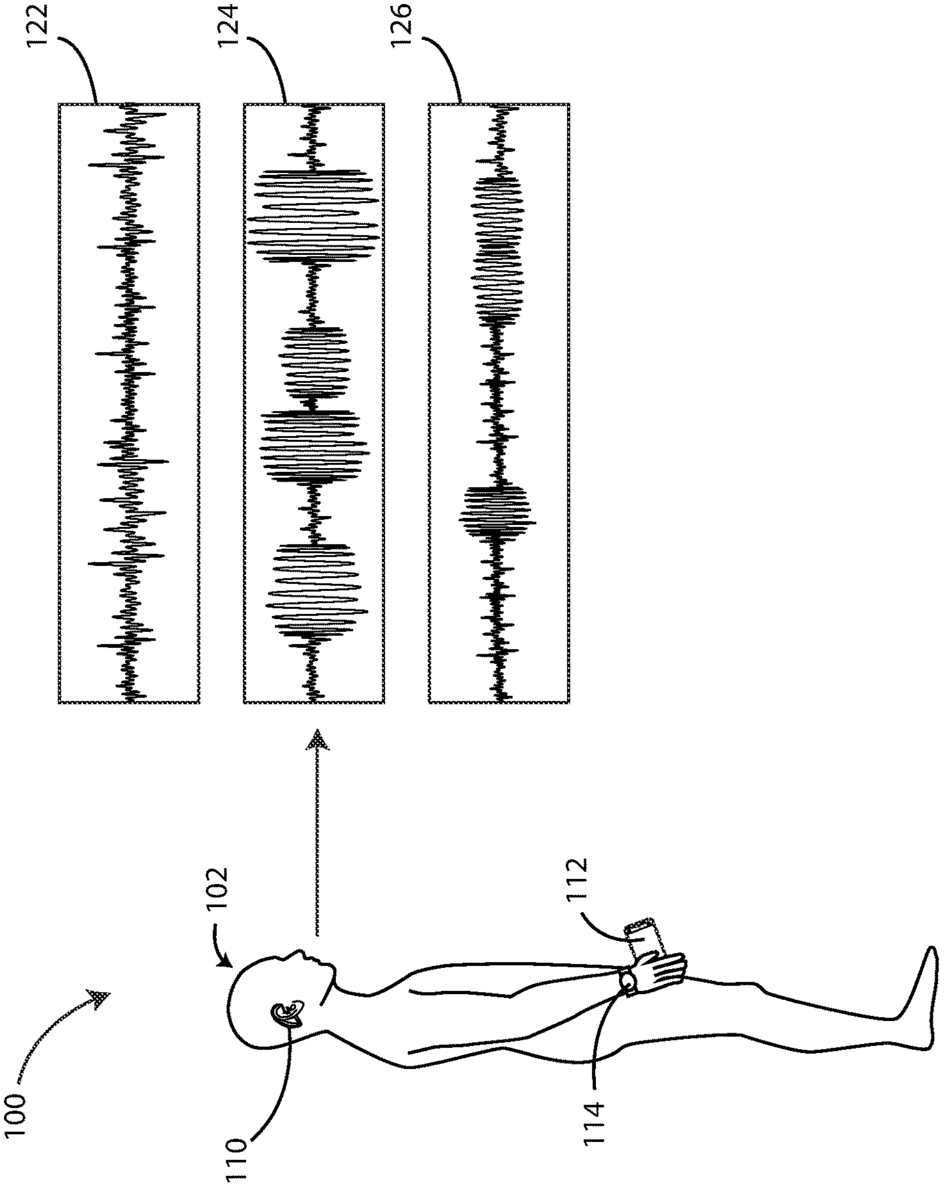
FIG. 1 is a schematic view of some components of a hearing assistance system in accordance with various embodiments herein.

Referring now to FIG. 1, a schematic view is shown of some components of a hearing assistance system 100 in accordance with various embodiments herein. FIG. 1 shows an ear-wearable device wearer 102 with an ear-wearable device 110. FIG. 1 also shows an example of an external accessory device 112 and, in this case, a smart watch 114. In some embodiments, the external accessory device 112 can specifically be a smart phone. In some embodiments, the smart watch 114 can serve as a type of external accessory device 112.

In various embodiments, the ear-wearable device 110 can include a control circuit and a microphone in electronic communication with the control circuit (various other possible components of ear-wearable devices here are described further below). As used herein, the term "microphone" shall include reference to all types of devices used to capture sounds including various types of microphones (including, but not limited to, carbon microphones, fiber optic microphones, dynamic microphones, electret microphones, ribbon microphones, laser microphones, condenser microphones, cardioid microphones, crystal microphones) and vibration sensors (including, but not limited to accelerometers and various types of pressure sensors). Microphones herein can include analog and digital microphones. Systems herein can also include various signal processing chips and components such as analog-to-digital converters and digital-to-analog converters. Systems herein can operate with audio data that is gathered, transmitted, and/or processed reflecting various sampling rates. By way of example, sampling rates used herein can include 8,000 Hz, 11,025 Hz, 16,000 Hz, 22,050 Hz, 32,000 Hz, 37,800 Hz, 44,056 Hz, 44,100 Hz, 47,250 Hz, 48,000 Hz, 50,000 Hz, 50,400 Hz, 64,000 Hz, 88,200 Hz, 96,000 Hz, 176,400 Hz, 192,000 Hz, or higher or lower, or within a range falling between any of the foregoing. Audio data herein can reflect various bit depths including, but not limited to 8, 16, and 24-bit depth.

In various embodiments, the ear-wearable device 110 can be configured to use a microphone or other noise or vibration sensor in order to gather sound data, such as in the form of signals from the microphone or other noise or vibration sensor It will be appreciated that sound collected by a microphone or other device can represent contributions from various sources of sound within a given environment. For example, the aggregate sound within an environment can include non-speech ambient sound 122 (background noise, which can be caused by equipment, vehicles, animals, devices, wind, etc.) as well as ear-wearable device wearer speech 124, and third-party speech 126.

In various embodiments, the ear-wearable device 110 can be configured to analyze the signals in order to identify sound representing speech. In various embodiments, the ear-wearable device 110 can be configured to analyze the signals in order to identify speech of the ear-wearable device wearer 102. Sound representing speech can be distinguished from general noise using various techniques as aided by signal processing algorithms and/or machine learning classification techniques, and can include aspects of phoneme recognition, frequency analysis, and evaluation of acoustic features such as those referenced below. In some embodiments, techniques for separating speech from background noise can be used including spectral subtraction, Wiener filtering, and mean-square error estimation. Spectral subtraction subtracts the power spectral density of the estimated interference from that of the mixture. The Wiener filter estimates clean speech from the ratios of speech spectrum and mixture spectrum. Mean-square error estimation models speech and noise spectra as statistically independent Gaussian random variables and estimates clean speech accordingly.

The speech of one individual can be distinguished from the speech of another individual using various techniques as aided by signal processing algorithms and/or machine learning classification techniques and can include analysis of various features including, but not limited to acoustic features. Features used herein for both distinguishing speech versus other noise and the speech of one individual from another individual can include both low-level and high-level features, and specifically can include low-level acoustic features including prosodic (such as fundamental frequency, speech rate, intensity, duration, energy, pitch, etc.), voice quality (such as format frequency and bandwidth, jitter and shimmer, glottal parameter, etc.), spectral (such as spectrum cut-off frequency, spectrum centroid, correlation density and mel-frequency energy, etc.), cepstral (such a Mel-Frequency Cepstral Coefficients (MFCCs), Linear Prediction Cepstral Coefficients (LPCC), etc.), and the like.

In various embodiments, the ear-wearable device 110 can be configured to do one or more of monitor signals from the microphone, analyze the signals in order to identify speech, and transmit data based on the signals representing the identified speech to a separate device. In various embodiments, the transmitted data can include continuous speech of at least about 1, 2, 3, 4, 5, 6, 7, 8, 9, 10, or 15 seconds or a duration falling within a range between any of the foregoing. In various embodiments, the transmitted data can include a total amount of speech (not necessarily all being continuous) equal to at least about 5, 10, 15, 20, 30, 45, 60, 120, or 180 seconds, or an amount falling within a range between any of the foregoing.

The ear-wearable device 110 can also gather other data regarding the ear-wearable device wearer. For example, the ear-wearable device 110 can use various sensors in order to gather data. Exemplary sensors are described in greater detail below. However, in some embodiments, the ear-wearable device 110 can include one or more of a motion sensor, a temperature sensor, a heart rate sensor, and a blood pressure sensor.

In some cases, the additional sensor data can be conveyed on to another device, such as along with the device-wearer speech related information. By way of example, in various embodiments, the ear-wearable device 110 can be further configured to gather motion sensor data and, in some cases, also transmit data based on motion sensor data to a separate device In various embodiments, the ear-wearable device 110 can be further configured to gather temperature sensor data and, in some cases, also transmit data based on temperature sensor data to a separate device. In various embodiments, the ear-wearable device 110 can be further configured to gather heart rate sensor data and, in some cases, transmit data based on heart rate sensor data to a separate. In various embodiments, the ear-wearable device 110 can be further configured to gather blood pressure sensor data and, in some cases, transmit data based on blood pressure sensor data to a separate device.

In some cases, signals/data from other sensors can be time-matched with the audio signals/data that are provided for analysis. However, in other embodiments, the signals/data from other sensors may not be time-matched with the audio signals/data. For example, in some embodiments, the signals/data from other sensors may reach backward in time to capture data relevant to the emotional status of the device wearer prior to the speech being evaluated. For example, if a person is becoming upset, this may be reflected first in a transient change in blood pressure data before the same is reflected in audio data. As such, in some embodiments, other sensor data can reflect a look-back period of about 1, 2, 3, 4, 5, 10, 15, 20, 30, 45, 60, 120, 180, 240, 300, 600 seconds, or longer, or an amount of time falling within a range between any of the foregoing.

In various embodiments, the external accessory device 112 (and/or another device such as smart watch 114) can be configured to extract features from the signals representing speech of the ear-wearable device wearer 102 and transmit the extracted features to a separate system or device for analysis of ear-wearable device wearer 102 emotion or status. However, in various embodiments, the external accessory device 112 itself can be configured to analyze the signals representing speech of the ear-wearable device wearer 102 in order to determine ear-wearable device wearer 102 emotion or status.

Features extracted herein (regardless of which device is performing the operation) can include low-level and high-level features. Features extracted herein can include, but are not limited to, low-level acoustic features including prosodic (such as fundamental frequency, speech rate, intensity, duration, energy, pitch, etc.), voice quality (such as format frequency and bandwidth, jitter and shimmer, glottal parameter, etc.), spectral (such as spectrum cut-off frequency, spectrum centroid, correlation density and mel-frequency energy, etc.), cepstral (such a Mel-Frequency Cepstral Coefficients (MFCCs), Linear Prediction Cepstral Coefficients (LPCC), etc.), and the like. In some embodiments, the open source toolkit OpenSmile can be used in order to extract features from acoustic data.

Emotions and status evaluated herein can include classifying the detected state or emotion in various ways. In some embodiments, a device wearer's state or emotion can be classified as being positive, neutral or negative. In some embodiments, a device wearer's state or emotion can be classified as happy, sad, angry, or neutral. In some embodiments, a device wearer's state or emotion can be classified as happy, sad, disgusted, scared, surprised, angry, or neutral. In some embodiments, in addition to or in replacement of other categorizations, a device wearer's state or emotion can be classified based on a level of detected stress. In some embodiments, a device wearer's state or emotion can be classified as highly stressed, stressed, normal stress, or low stress. In some embodiments, a discrete emotion description model can be used and in other embodiments a continuous emotion description model can be used. In some embodiments, a two-dimensional arousal-valence model can be used for classification. Many different specific classifications are contemplated herein.

Status evaluated herein is not limited to emotion and stress. In various embodiments, status herein can include other states impacting sounds created by the device wearer. By way of example, the process of breathing can generate sound which can be analyzed herein in order to derive information regarding the status of the device wearer. Thus, in various embodiments, the ear-wearable device wearer 102 status can include a breathing status. In various embodiments, the breathing status can include a breathing pattern consistent with sleep apnea, COPD, or another disease state.

Figure 2:
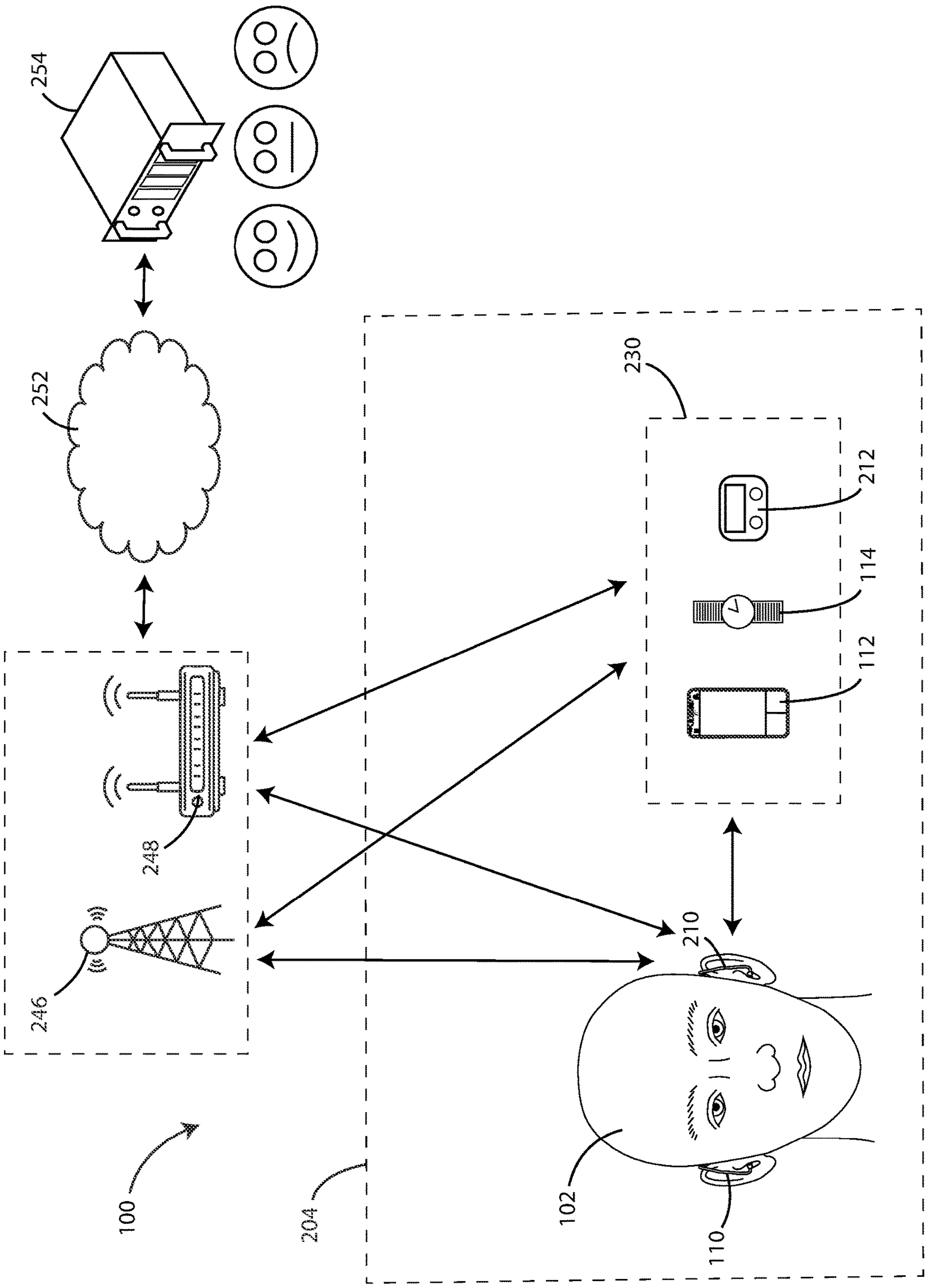
FIG. 2 is a schematic view of some components of a hearing assistance system in accordance with various embodiments herein.

Referring now to FIG. 2, a schematic view of components of a hearing assistance system 100 is shown in accordance with various embodiments herein. In specific, FIG. 2 shows an ear-wearable device wearer 102 within a local environment 204. The hearing assistance system 100 includes an ear-wearable device 110. In this case, the hearing assistance system 100 also includes a second ear-wearable device 210. The hearing assistance system 100 also includes a separate device 230 (or devices). The separate device 230 can be in electronic communication with at least one of the ear-wearable devices 110, 210. The separate device 230 can include one or more of an external accessory device 112, a smart watch 114, another type of accessory device 212, or the like.

In various embodiments, the separate device 230 can be configured to analyze the signals in order to identify speech of the ear-wearable device wearer 102. However, in other embodiments, at least one of the ear-wearable devices (110, 210) can analyze the signals in order to identify speech of the ear-wearable device wearer 102.

In some embodiment, the separate device 230 can also be in communication with other devices. In some embodiment, the separate device 230 can convey data to other devices, such as to allow other devices or system to perform the analysis of the data to determine emotion or state. In some embodiment, the separate device 230 can serve as a data communication gateway. For example, in the example of FIG. 2, the hearing assistance system can be in communication with a cell tower 246 and/or a WIFI router 248. The cell tower 246 and/or the WIFI router 248 can be part of and/or provide a link to a data communication network. In some embodiments, the cell tower 246 and/or the WIFI router 248 can provide communication with the cloud 252. One or more servers 254 (real or virtual) can be in the cloud 252 or accessible through the cloud 252 in order to provide data processing power, data storage, emotion and/or state analysis and the like.

In some embodiments, emotion and/or state analysis can be performed through an API taking information related to speech and an input and providing information regarding emotion and/or state as an output. In various embodiments, emotion and/or state analysis can be performed using a machine learning approach. More specifically, in various embodiments, emotion and/or state analysis can be performed using a support vector machine (SVM) approach, a linear discriminant analysis (LDA) model, a multiple kernel learning (MKL) approach, a deep neural network approach. In various embodiments, fusion methods can be used as a part of analysis herein including, but not limited to feature-level fusion (or early fusion), model-level fusion (or middle fusion), and decision-level fusion (or late fusion).

In various embodiments, information regarding emotion and/or state can be passed back to the separate device 230 and/or the ear-wearable devices 110, 210. In various embodiments, the external accessory device 112 is configured to extract features from the signals representing speech of the ear-wearable device wearer 102 and transmit the extracted features on (such as to a server 254) for analysis of ear-wearable device wearer 102 emotion or state. In various embodiments, the extracted features do not include words.

Figure 3:
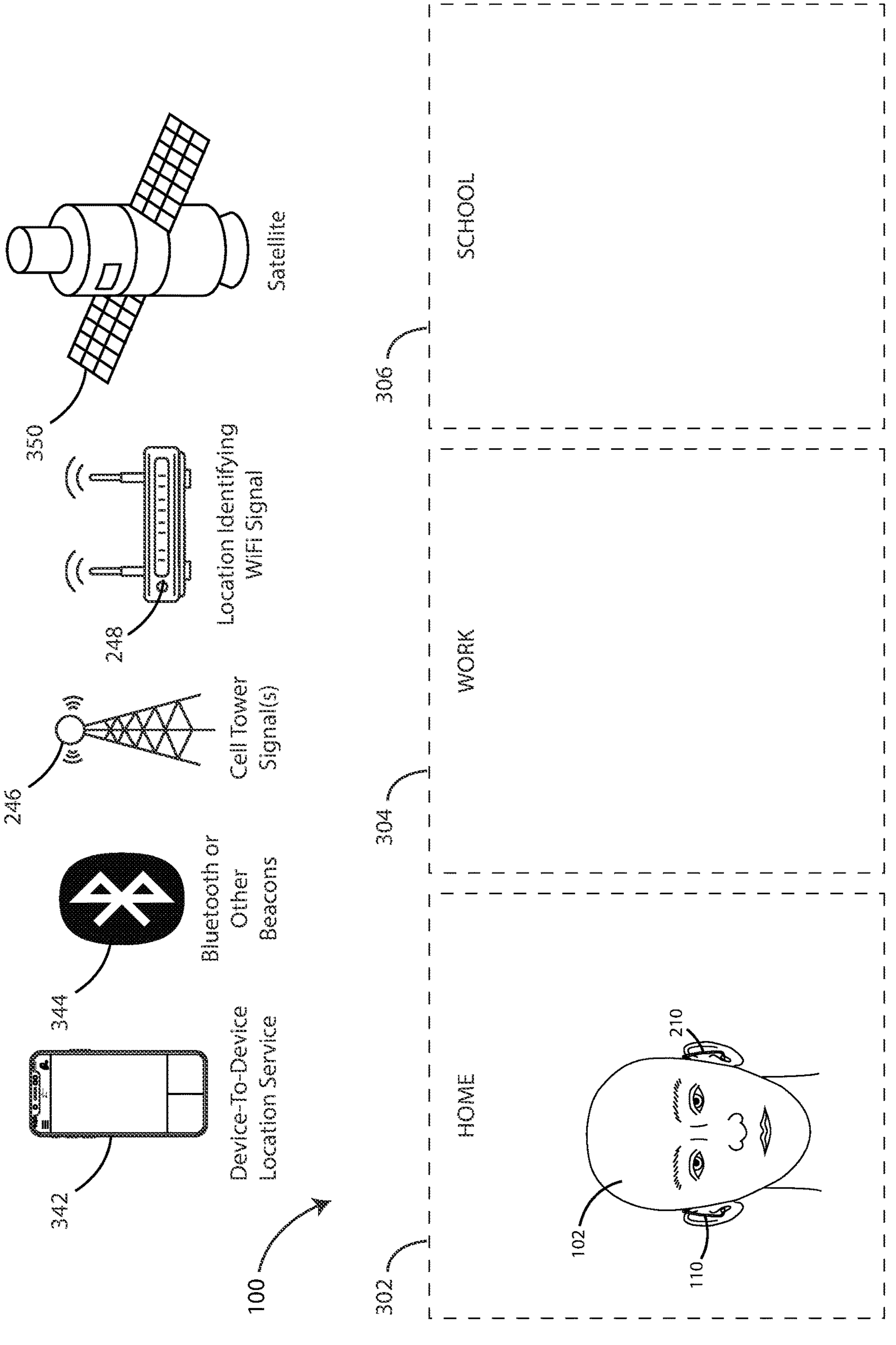
FIG. 3 is a schematic view of some components of a hearing assistance system in accordance with various embodiments herein.

In accordance with various embodiments herein, information regarding geospatial location can be used in order to further interpret the device wearer's emotion or state as well as provide information regarding the relationship between geospatial location and observed emotion or state. In various embodiments herein, the ear-wearable devices 110, 210, and/or an accessory device thereto can be used to interface with a system or component in order to determine geospatial location. Referring now to FIG. 3, a schematic view of components of a hearing assistance system 100 is shown in accordance with various embodiments herein. FIG. 3 shows an ear-wearable device wearer 102 within a home environment 302, which can serve as an example of a geospatial location. However, the ear-wearable device wearer 102 can also move to other geospatial locations representing other embodiments. For example, FIG. 3 also shows a work environment 304 and a school environment 306.

As previously stated, the ear-wearable devices 110, 210, and/or an accessory device thereto can be used to interface with a system or component in order to determine geospatial location. For example, the ear-wearable devices 110, 210, and/or an accessory device thereto can be used to interface with a locating device 342, a BLUETOOTH beacon 344, a cell tower 246, a WIFI router 248, a satellite 350, or the like. In various embodiments, the system can be configured with data cross referencing specific geospatial coordinates with environments of relevant for the individual device wearer.

Figure 4:
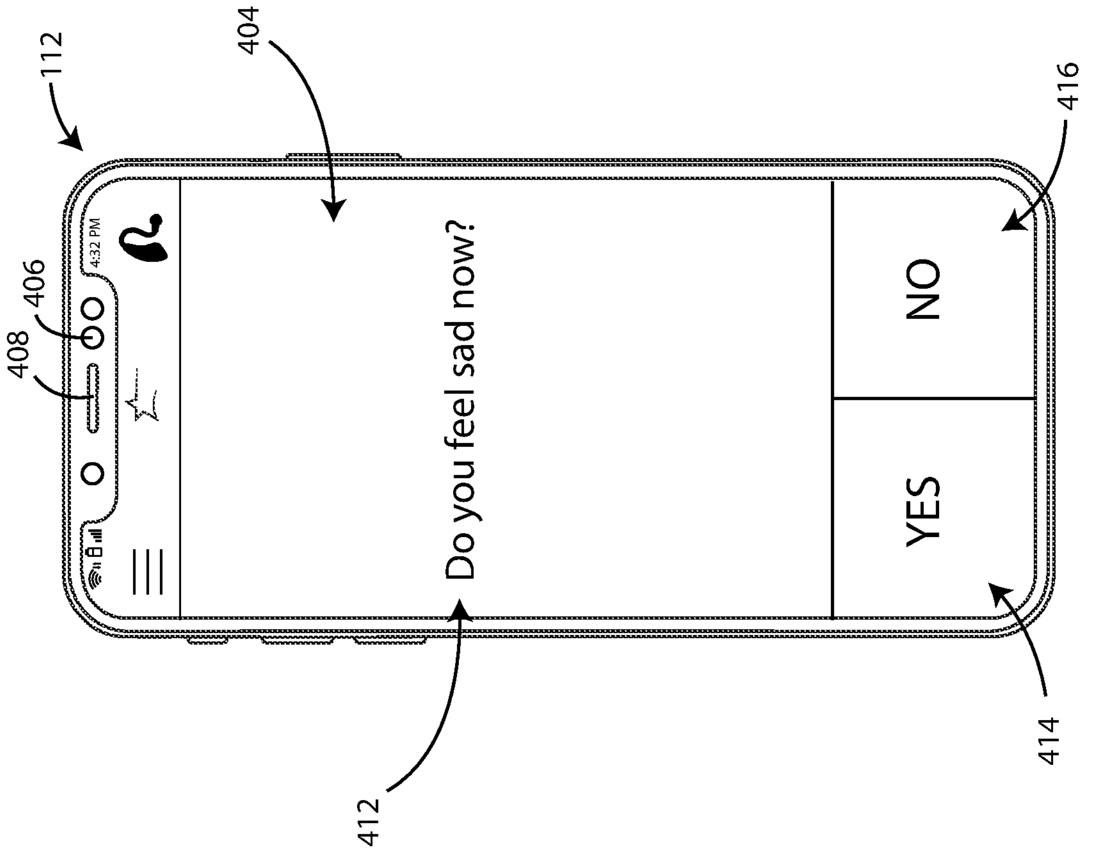
FIG. 4 is a schematic view of an external accessory device in accordance with various embodiments herein.

Referring now to FIG. 4, a schematic view of an external accessory device 112 is shown in accordance with various embodiments herein. The external accessory device 112 includes a display screen 404. In some embodiments, the external accessory device 112 can also include a camera 406 and a speaker 408

The external accessory device 112 can be used to interface with the ear-wearable device wearer. For example, the external accessory device 112 can display a query 412 on the display screen 404. In some embodiments, the query 412 can be used to confirm or calibrate emotion or status detected through evaluation of device wearer speech. For example, the query could state "do you feel sad now?" in order to confirm that emotional state of the device wearer is one of sadness. The external accessory device 112 can also include various user interface objects on the display screen 404, such as a first user input button 414 and a second user input button 416.

In various embodiments, the display screen 404 can be used to display information to the device wearer and/or to a third party. The displayed information can include the results of emotion and/or state analysis as well as aggregated forms of the same and/or how the emotion and/or state data changes over time or correlates with other pieces of data such as geolocation data. FIGS. 5-8 provide some examples of information that can be displayed, but it must be emphasized that these are merely a few examples and that many other examples are contemplated herein.

Data reflecting detected emotions can be displayed/evaluated as a function of different time periods such as hourly, daily, weekly, monthly, yearly trend and the like.

In some embodiments, certain patterns reflecting on an underlying status or condition may be more easily identified by looking at trends over a particular time frame. For example, viewing how data changes over a day may allow for easier recognition of status or conditions having a circadian type rhythm whereas viewing how data changes over a year may allow for easier recognition of a status or condition that may be impacted by the time of year such as seasonal affective disorder or the like.

Other types of data can be combined with emotion/status data in order to provide insight into what may be triggering certain emotions or status. For example, in accordance with various embodiments herein, geospatial data can be gathered and referenced against emotion or status data in order to show the effects of geospatial location (and/or aspects or conditions within given environments) on emotion or status.

In various embodiments herein, data regarding emotions/status can be saved and aggregated in order to provide further insight into a device wearer's emotional state or other status.

Figure 5:
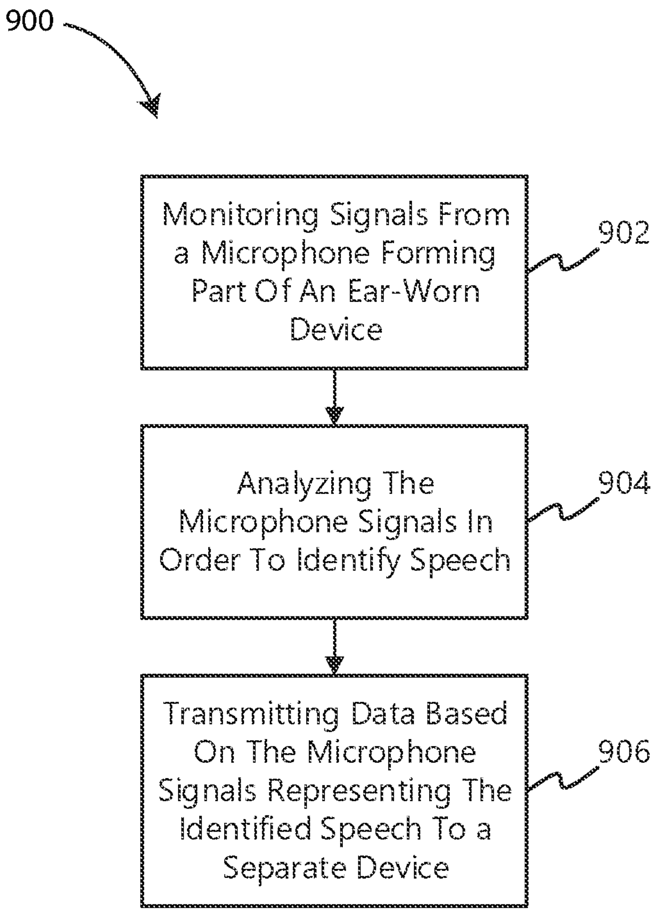
FIG. 5 is a schematic view of operations of a method in accordance with various embodiments herein.

Embodiments herein include various methods. Referring now to FIG. 5, a schematic view is shown of operations of a method in accordance with various embodiments herein. The method 900 can include an operation of monitoring 902 signals from a microphone forming part of an ear-wearable device. The method can also include an operation of analyzing 904 the microphone signals in order to identify speech. The method can also include an operation of transmitting 906 data based on the microphone signals representing the identified speech to a separate device.

Figure 6:
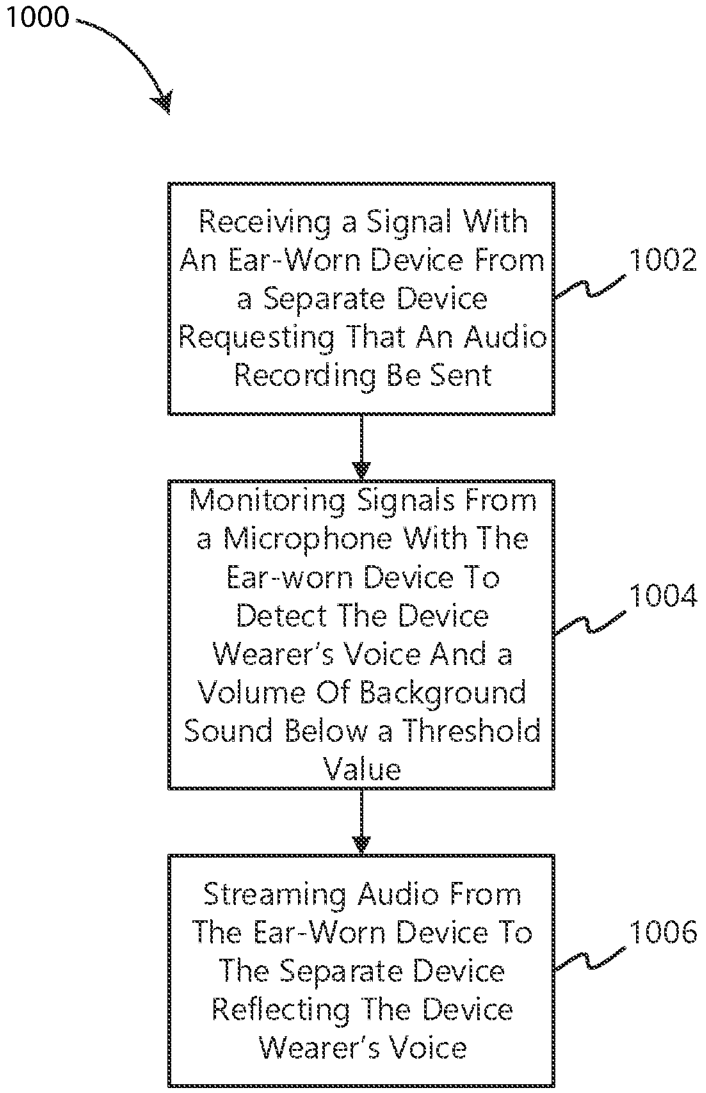
FIG. 6 is a schematic view of operations of a method in accordance with various embodiments herein.

Referring now to FIG. 6, a schematic view is shown of operations of a method in accordance with various embodiments herein. The method 1000 can include an operation of receiving 1002 a signal with the ear-wearable device from the separate device requesting that data based on the microphone signals be sent from the ear-wearable device to the separate device. The method can include an operation of monitoring 1004 signals from a microphone with the ear-wearable device to detect the device wearer's voice and a volume of background sound below a threshold value. Various amounts of background sound can be used as a threshold value. In some embodiments, the threshold for background sound can be about 5, 10, 15, 20, 25, 30, 35, 40, 45, 50, 55, or 60 db, or a volume falling within a range between any of the foregoing. The method can include an operation of streaming 1006 audio from the ear-wearable device to the separate device reflecting the device wearer's voice.

Figure 7:
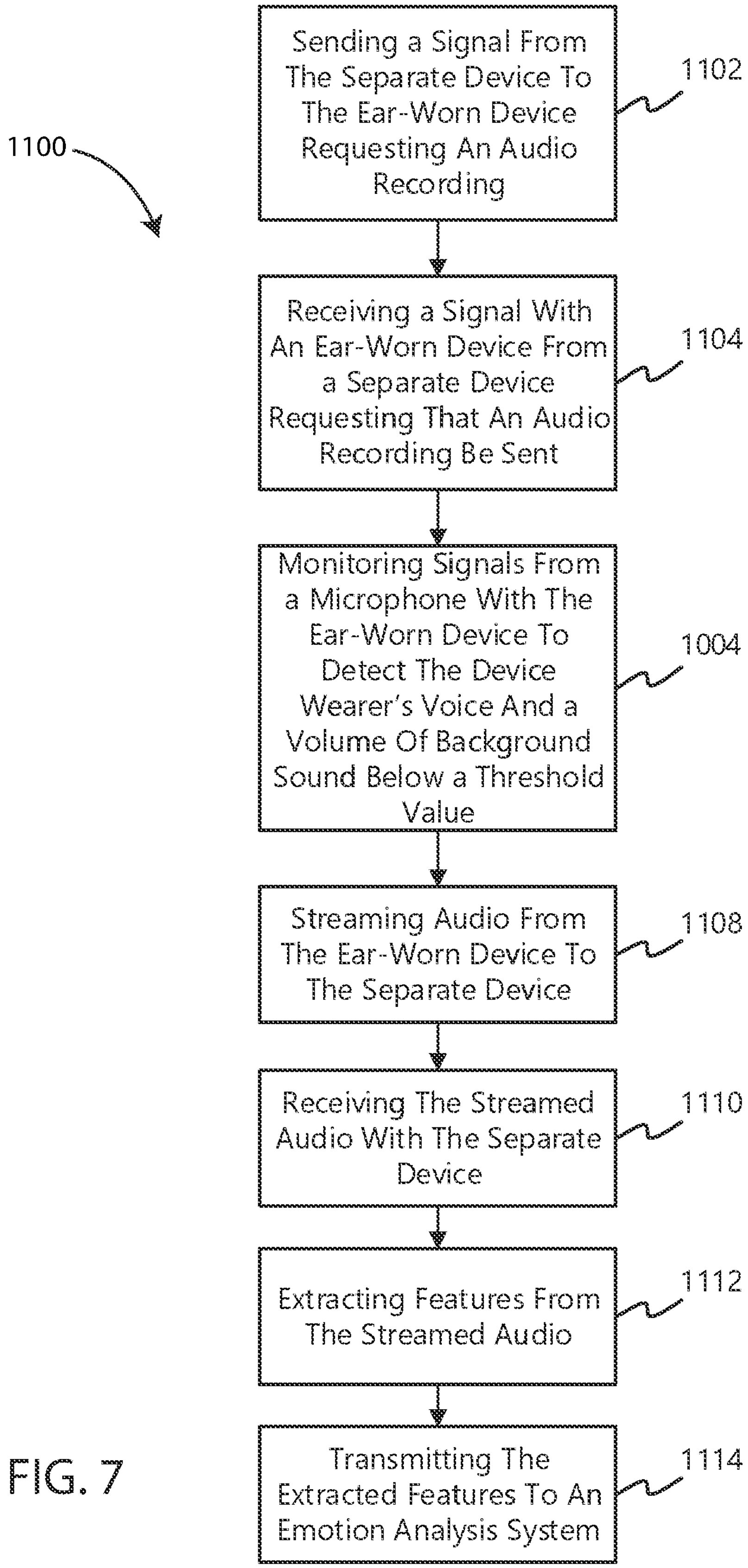
FIG. 7 is a schematic view of operations of a method in accordance with various embodiments herein.

Referring now to FIG. 7, a schematic view is shown of operations of a method 1100 in accordance with various embodiments herein. The method can include an operation of sending 1102 a signal from the separate device to the ear-wearable device requesting an audio recording. In various embodiments, the separate device 230 sends a signal to the ear-wearable device 110 requesting an audio recording from 10 to 50 times per day. The method can include an operation of receiving 1104 a signal with an ear-wearable device from a separate device requesting that an audio recording be sent. While not intending to be bound by theory, it is believed that sending an audio recording (typically a streaming operation) can consume significant amounts of energy and therefore can act as a significant drain on the batter of the ear-wearable device. Thus, streaming audio at only discrete times (such as when the separate device requests it) can function to conserve the battery life of the ear-wearable device.

The method can include an operation of monitoring 1004 signals from a microphone with the ear-wearable device to detect the device wearer's voice and a volume of background sound below a threshold value. The method can include an operation of streaming audio from the ear-wearable device to the separate device 1108. The method can include an operation of receiving 1110 the streamed audio with the separate device. The method can include an operation of extracting 1112 features from the streamed audio. The method can include an operation of transmitting 1114 the extracted features to an emotion analysis system.

Figure 8:
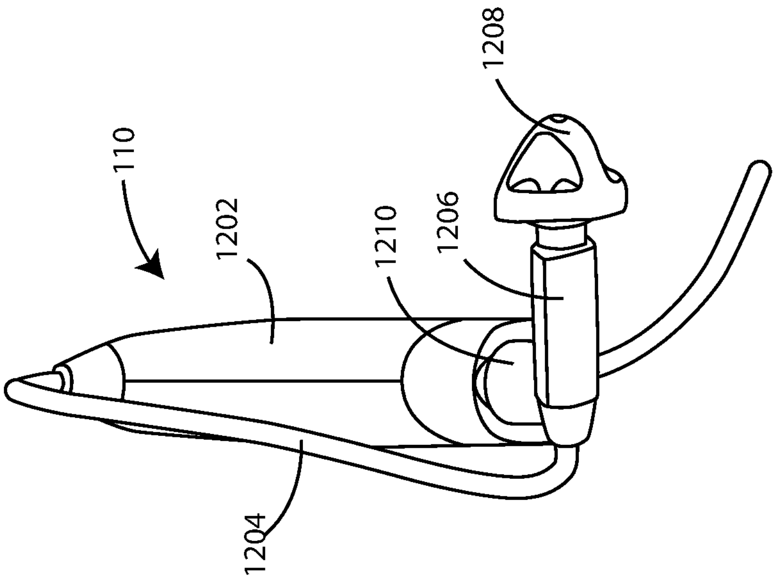
FIG. 8 is a schematic view of an ear-wearable device in accordance with various embodiments herein.

Referring now to FIG. 8, a schematic view of an ear-wearable device 110 is shown in accordance with various embodiments herein. The ear-wearable device 110 can include a hearing device housing 1202. The hearing device housing 1202 can define a battery compartment 1210 into which a battery can be disposed to provide power to the device. The ear-wearable device 110 can also include a receiver 1206 adjacent to an earbud 1208. The receiver 1206 an include a component that converts electrical impulses into sound, such as an electroacoustic transducer, speaker, or loud speaker. Such components can be used to generate an audible stimulus in various embodiments herein. A cable 1204 or connecting wire can include one or more electrical conductors and provide electrical communication between components inside of the hearing device housing 1202 and components inside of the receiver 1206.

The ear-wearable device 110 shown in FIG. 8 is a receiver-in-canal type device and thus the receiver is designed to be placed within the ear canal. However, it will be appreciated that many different form factors for ear-wearable devices are contemplated herein. As such, ear-wearable devices herein can include, but are not limited to, behind-the-ear (BTE), in-the ear (ITE), in-the-canal (ITC), invisible-in-canal (IIC), receiver-in-canal (MC), receiver in-the-ear (RITE) and completely-in-the-canal (CIC) type hearing assistance devices.

The term "ear-wearable device" shall also refer to devices that can produce optimized or processed sound for persons with normal hearing. Ear-wearable devices herein can include hearing assistance devices. In some embodiments, the ear-wearable device can be a hearing aid falling under 21 C.F.R. § 801.420. In another example, the ear-wearable device can include one or more Personal Sound Amplification Products (PSAPs). In another example, the ear-wearable device can include one or more cochlear implants, cochlear implant magnets, cochlear implant transducers, and cochlear implant processors. In another example, the ear-wearable device can include one or more "hearable" devices that provide various types of functionality. In other examples, ear-wearable devices can include other types of devices that are wearable in, on, or in the vicinity of the user's ears. In other examples, ear-wearable devices can include other types of devices that are implanted or otherwise osseointegrated with the user's skull; wherein the device is able to facilitate stimulation of the wearer's ears via the bone conduction pathway.

Ear-wearable devices of the present disclosure can incorporate an antenna arrangement coupled to a high-frequency radio, such as a 2.4 GHz radio. The radio can conform to an IEEE 802.11 (e.g., WIFI) or BLUETOOTH® (e.g., BLE, BLUETOOTH® 4.2 or 5.0) specification, for example. It is understood that ear-wearable devices of the present disclosure can employ other radios, such as a 900 MHz radio. Ear-wearable devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED) or other electronic device that serves as a source of digital audio data or files.

Figure 9:
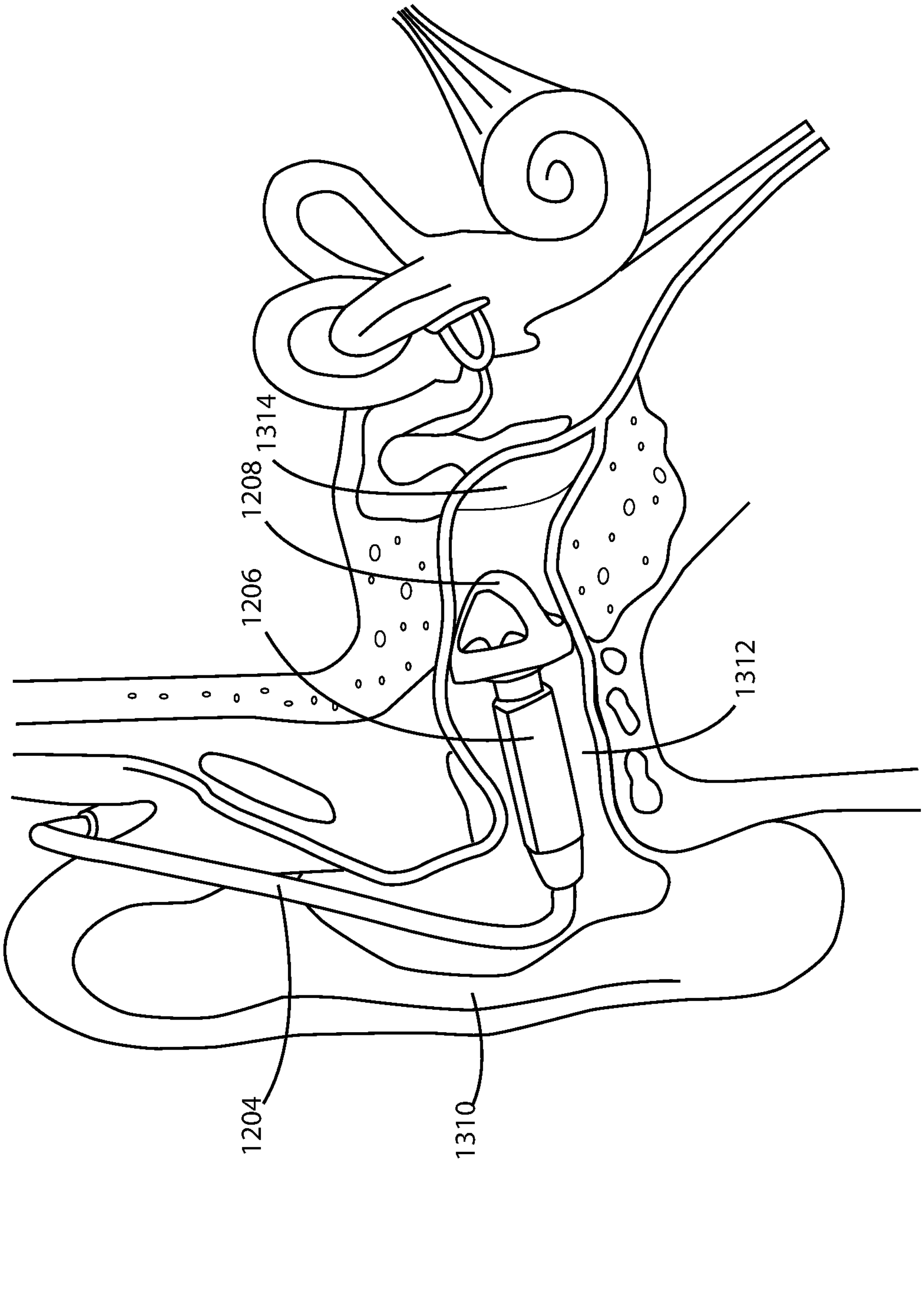
FIG. 9 is a schematic view of an ear-wearable device within an ear of a device wearer in accordance with various embodiments herein.

As mentioned above, the ear-wearable device 110 shown in FIG. 8 can be a receiver-in-canal type device and thus the receiver is designed to be placed within the ear canal. Referring now to FIG. 9, a schematic view is shown of an ear-wearable device 110 disposed within the ear of a subject in accordance with various embodiments herein. In this view, the receiver 1206 and the earbud 1208 are both within the ear canal 1312, but do not directly contact the tympanic membrane 1314. The hearing device housing is mostly obscured in this view behind the pinna 1310, but it can be seen that the cable 1204 passes over the top of the pinna 1310 and down to the entrance to the ear canal 1312.

Figure 10:
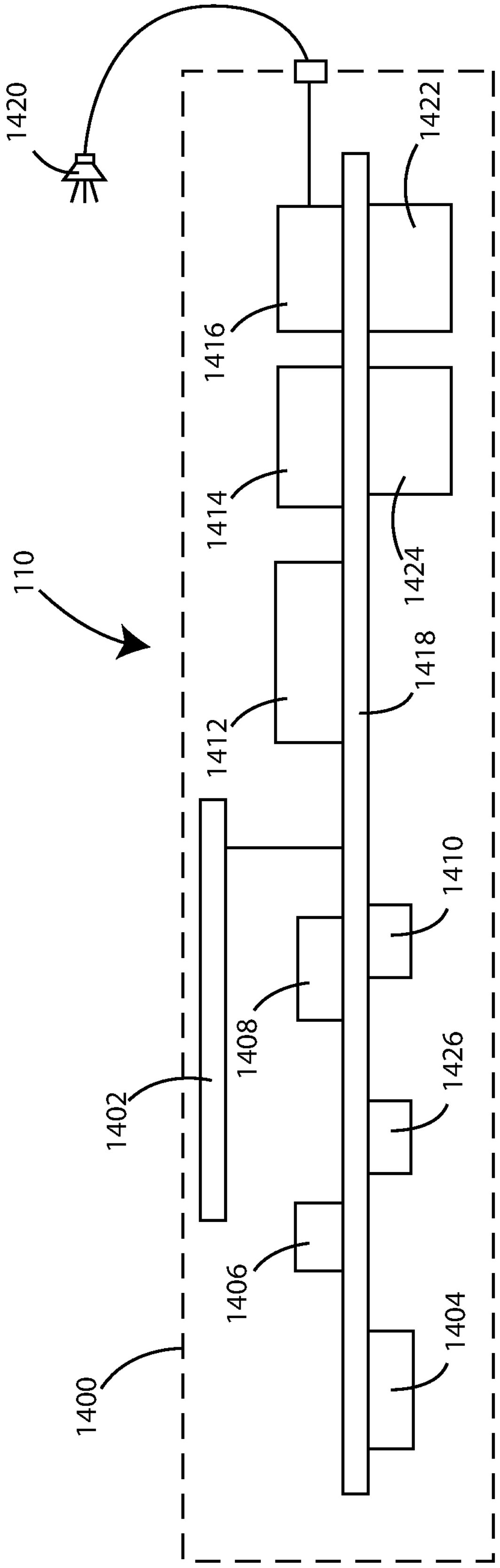
FIG. 10 is a schematic block diagram of components of an ear-wearable device in accordance with various embodiments herein.

Referring now to FIG. 10, a schematic block diagram of components of an ear-wearable device is shown in accordance with various embodiments herein. The block diagram of FIG. 10 represents a generic ear-wearable device for purposes of illustration. The ear-wearable device 110 shown in FIG. 10 includes several components electrically connected to a flexible mother circuit 1418 (e.g., flexible mother board) which is disposed within housing 1400. A power supply circuit 1404 can include a battery and can be electrically connected to the flexible mother circuit 1418 and provides power to the various components of the ear-wearable device 110. One or more microphones 1406 are electrically connected to the flexible mother circuit 1418, which provides electrical communication between the microphones 1406 and a digital signal processor (DSP) 912. Among other components, the DSP 1412 incorporates or is coupled to audio signal processing circuitry configured to implement various functions described herein. A sensor package 1414 can be coupled to the DSP 1412 via the flexible mother circuit 1418. The sensor package 1414 can include one or more different specific types of sensors such as those described in greater detail below. One or more user switches 1410 (e.g., on/off, volume, mic directional settings) are electrically coupled to the DSP 141 via the flexible mother circuit 1418.

An audio output device 1416 is electrically connected to the DSP 1412 via the flexible mother circuit 1418. In some embodiments, the audio output device 1416 comprises a speaker (coupled to an amplifier). In other embodiments, the audio output device 1416 comprises an amplifier coupled to an external receiver 1420 adapted for positioning within an ear of a wearer. The external receiver 1420 can include an electroacoustic transducer, speaker, or loud speaker. The ear-wearable device 110 may incorporate a communication device 1408 coupled to the flexible mother circuit 1418 and to an antenna 1402 directly or indirectly via the flexible mother circuit 1418. The communication device 1408 can be a BLUETOOTH® transceiver, such as a BLE (BLUETOOTH® low energy) transceiver or other transceiver(s) (e.g., an IEEE 802.11 compliant device). The communication device 1408 can be configured to communicate with one or more external devices, such as those discussed previously, in accordance with various embodiments. In various embodiments, the communication device 1408 can be configured to communicate with an external visual display device such as a smart phone, a video display screen, a tablet, a computer, or the like.

In various embodiments, the ear-wearable device 110 can also include a control circuit 1422 and a memory storage device 1424. The control circuit 1422 can be in electrical communication with other components of the device. In some embodiments, a clock circuit 1426 can be in electrical communication with the control circuit. The control circuit 1422 can execute various operations, such as those described herein. The control circuit 1422 can include various components including, but not limited to, a microprocessor, a microcontroller, an FPGA (field-programmable gate array) processing device, an ASIC (application specific integrated circuit), or the like. The memory storage device 1424 can include both volatile and non-volatile memory. The memory storage device 1424 can include ROM, RAM, flash memory, EEPROM, SSD devices, NAND chips, and the like. The memory storage device 1424 can be used to store data from sensors as described herein and/or processed data generated using data from sensors as described herein.

It will be appreciated that various of the components described in FIG. 10 can be associated with separate devices and/or accessory devices to the ear-wearable device. By way of example, microphones can be associated with separate devices and/or accessory devices. Similarly, audio output devices can be associated with separate devices and/or accessory devices to the ear-wearable device.

Accessory devices herein can include various different components. In some embodiments, the accessory device can be a personal communications device, such as a smartphone. However, the accessory device can also be other things such as a wearable device, a handheld computing device, a dedicated location determining device (such as a handheld GPS unit), or the like.

Figure 11:
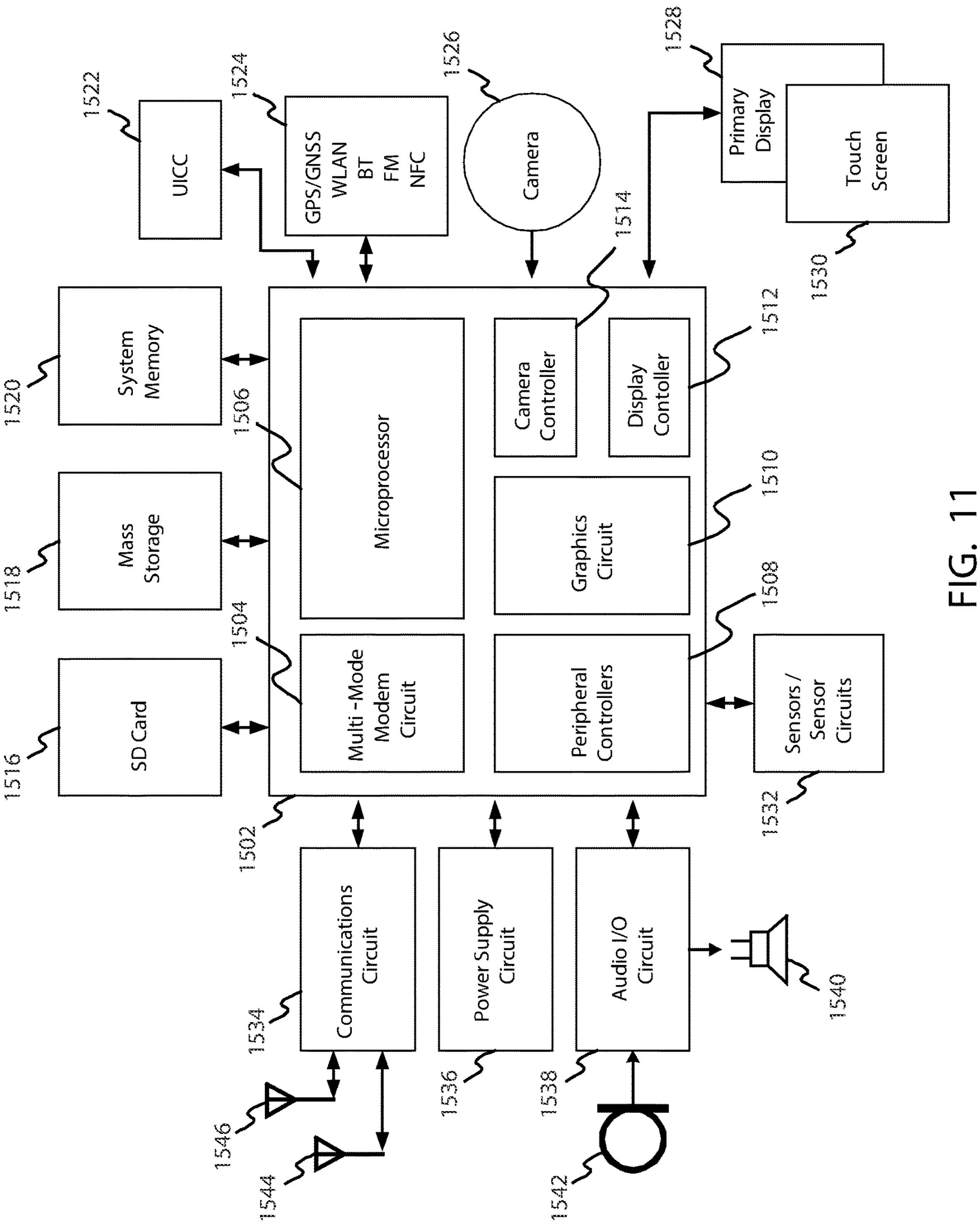
FIG. 11 is a schematic block diagram of components of an exemplary accessory device in accordance with various embodiments herein.

Referring now to FIG. 11, a schematic block diagram is shown of components of an accessory device (which could be a personal communications device or another type of accessory device) in accordance with various embodiments herein. This block diagram is just provided by way of illustration and it will be appreciated that accessory devices can include greater or lesser numbers of components. The accessory device in this example can include a control circuit 1502. The control circuit 1502 can include various components which may or may not be integrated. In various embodiments, the control circuit 1502 can include a microprocessor 1506, which could also be a microcontroller, FPGA, ASIC, or the like. The control circuit 1502 can also include a multi-mode modem circuit 1504 which can provide communications capability via various wired and wireless standards. The control circuit 1502 can include various peripheral controllers 1508. The control circuit 1502 can also include various sensors/sensor circuits 1532. The control circuit 1502 can also include a graphics circuit 1510, a camera controller 1514, and a display controller 1512. In various embodiments, the control circuit 1502 can interface with an SD card 1516, mass storage 1518, and system memory 1520. In various embodiments, the control circuit 1502 can interface with universal integrated circuit card (UICC) 1522. A spatial location determining circuit can be included and can take the form of an integrated circuit 1524 that can include components for receiving signals from GPS, GLONASS, BeiDou, Galileo, SBAS, WLAN, BT, FM, and NFC type protocols. In various embodiments, the accessory device can include a camera 1526. In various embodiments, the control circuit 1502 can interface with a primary display 1528 that can also include a touch screen 1530. In various embodiments, an audio I/O circuit 1538 can interface with the control circuit 1502 as well as a microphone 1542 and a speaker 1540. In various embodiments, a power supply circuit 1536 can interface with the control circuit 1502 and/or various other circuits herein in order to provide power to the system. In various embodiments, a communications circuit 1534 can be in communication with the control circuit 1502 as well as one or more antennas (1544, 1546).

Sensors

Ear-wearable devices herein can include one or more sensor packages (including one or more discrete or integrated sensors) to provide data. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. The IMU can be of a type disclosed in commonly owned U.S. patent application Ser. No. 15/331,230, filed Oct. 21, 2016, which is incorporated herein by reference. In some embodiments, electromagnetic communication radios or electromagnetic field sensors (e.g., telecoil, NFMI, TMR, GME, etc.) sensors may be used to detect motion or changes in position. In some embodiments, biometric sensors may be used to detect body motions or physical activity. Motions sensors can be used to track movement of a patient in accordance with various embodiments herein.

In some embodiments, the motion sensors can be disposed in a fixed position with respect to the head of a patient, such as worn on or near the head or ears. In some embodiments, the operatively connected motion sensors can be worn on or near another part of the body such as on a wrist, arm, or leg of the patient.

According to various embodiments, the sensor package can include one or more of a motion sensor, (e.g., IMU, and accelerometer (3, 6, or 9 axis), a gyroscope, a barometer, an altimeter, a magnetometer, a magnetic sensor, an eye movement sensor, a pressure sensor), an acoustic sensor, a telecoil, a heart rate sensor, a global positioning system (GPS), a barometer, a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-wearable device. However, in some embodiments, the sensor packages can include one or more additional sensors that are external to an ear-wearable device. For example, various of the sensors described above can be part of a wrist-wearable or ankle-wearable sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers and gyroscopes (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the ear-wearable device. In addition to the external sensors discussed hereinabove, the sensor package can comprise a network of body sensors (such as those listed above) that sense movement of a multiplicity of body parts (e.g., arms, legs, torso). In some embodiments, the ear-wearable device can be in electronic communication with the sensors or processor of a medical device (implantable, wearable, external, etc.).

Methods

Aspects of system/device operation described elsewhere herein can be performed as operations of one or more methods in accordance with various embodiments herein. Likewise, operations of methods described herein can be implemented as configurations of systems/devices in accordance with various embodiments herein.

In an embodiment, a method of monitoring anxiety with an ear-wearable device is included, the method can include monitoring signals from a microphone, identifying signs of anxiety in the microphone signals, and providing a wearer of the ear-wearable device with feedback related to the identified anxiety. In an embodiment of the method, the signs of anxiety include at least one of tonal change, volume change, and change of vocal cadence.

In an embodiment of the method, feedback provided by the device or system can include suggested anxiety interventions. Many different anxiety interventions are contemplated herein including, but not limited to, breathing instructions. Breathing instructions can include breathing cadence, breathing depth, and the like. Anxiety interventions herein can also include meditation instructions and/or playing a calming audio stream. In an embodiment of the method, the feedback comprises auditory feedback that indicates that anxiety was identified and provides suggested anxiety interventions.

In an embodiment, the method can further include monitoring signals from a sensor package to identify signs of anxiety, wherein the sensor package includes at least one selected from the group consisting of a motion sensor, a heart rate sensor, a temperature sensor, a respiratory rate sensor, and an SpO2 sensor. In an embodiment of the method, signs of anxiety include a change in microphone signals along with a change in signals from at least one sensor in the sensor package.

In an embodiment, the method can further include analyzing signals from the microphone in order to identify speech of a wearer of the ear-wearable device. In an embodiment of the method, the signs of anxiety can include a change in the speech of the wearer of the ear-wearable device.

In an embodiment of the method, the ear-wearable device is configured to determine a baseline value of anxiety for a wearer of the ear-wearable device. In an embodiment of the method, the baseline value accounts for at least one of language, culture, and persona of the wearer of the ear-wearable device.

In an embodiment, the method can further include transmitting data based on microphone signals to a separate device. In an embodiment, the separate device can include an external accessory device.

Further Embodiments

Embodiments herein relate to embodiments herein relate to ear-wearable device systems and methods for monitoring a device wearer's emotional state and status. In a first aspect, a hearing assistance system is included having an ear-wearable device can include a control circuit, and a microphone in electronic communication with the control circuit. The ear-wearable device can be configured to monitor signals from the microphone, analyze the signals in order to identify speech, and transmit data based on the signals representing the identified speech to a separate device.

In a second aspect, in addition to one or more of the preceding or following aspects, or in the alternative to some aspects, the ear-wearable device is configured to analyze the signals in order to identify speech of the ear-wearable device wearer.

In a third aspect, in addition to one or more of the preceding or following aspects, or in the alternative to some aspects, the separate device is configured to analyze the signals in order to identify speech of the ear-wearable device wearer.

In a fourth aspect, in addition to one or more of the preceding or following aspects, or in the alternative to some aspects, the separate device includes an external accessory device.

In a fifth aspect, in addition to one or more of the preceding or following aspects, or in the alternative to some aspects, the external accessory device is configured to extract features from the signals representing speech of the ear-wearable device wearer and transmit the extracted features to a separate device for analysis of ear-wearable device wearer emotion.

In a sixth aspect, in addition to one or more of the preceding or following aspects, or in the alternative to some aspects, the extracted features do not include words.

In a seventh aspect, in addition to one or more of the preceding or following aspects, or in the alternative to some aspects, the external accessory device is configured to analyze the signals representing speech of the ear-wearable device wearer in order to determine ear-wearable device wearer emotion.

In an eighth aspect, in addition to one or more of the preceding or following aspects, or in the alternative to some aspects, a system further can include receiving information back from the separate device regarding the emotional state of the device wearer.

In a ninth aspect, in addition to one or more of the preceding or following aspects, or in the alternative to some aspects, the ear-wearable device further can include a motion sensor.

In a tenth aspect, in addition to one or more of the preceding or following aspects, or in the alternative to some aspects, the ear-wearable device is further configured to transmit data based on motion sensor data to a separate device.

In an eleventh aspect, in addition to one or more of the preceding or following aspects, or in the alternative to some aspects, the system is configured to extract features from the microphone signals representing speech of the ear-wearable device wearer and transmit the extracted features along with data based on the motion sensor to a separate device for analysis of ear-wearable device wearer emotion.

In a twelfth aspect, in addition to one or more of the preceding or following aspects, or in the alternative to some aspects, the ear-wearable device further can include a temperature sensor.

In a thirteenth aspect, in addition to one or more of the preceding or following aspects, or in the alternative to some aspects, the ear-wearable device is further configured to transmit data based on temperature sensor data to a separate device.

In a fourteenth aspect, in addition to one or more of the preceding or following aspects, or in the alternative to some aspects, the system is configured to extract features from the microphone signals representing speech of the ear-wearable device wearer and transmit the extracted features along with data based on the temperature sensor to a separate device for analysis of ear-wearable device wearer emotion.

In a fifteenth aspect, in addition to one or more of the preceding or following aspects, or in the alternative to some aspects, the ear-wearable device further can include a heart rate sensor.

In a sixteenth aspect, in addition to one or more of the preceding or following aspects, or in the alternative to some aspects, the ear-wearable device is further configured to transmit data based on heart rate sensor data to a separate device.

In a seventeenth aspect, in addition to one or more of the preceding or following aspects, or in the alternative to some aspects, the system is configured to extract features from the microphone signals representing speech of the ear-wearable device wearer and transmit the extracted features along with data based on the heart rate sensor to a separate device for analysis of ear-wearable device wearer emotion.

In an eighteenth aspect, in addition to one or more of the preceding or following aspects, or in the alternative to some aspects, the ear-wearable device further can include a blood pressure sensor.

In a nineteenth aspect, in addition to one or more of the preceding or following aspects, or in the alternative to some aspects, the ear-wearable device is further configured to transmit data based on blood pressure sensor data to a separate device.

In a twentieth aspect, in addition to one or more of the preceding or following aspects, or in the alternative to some aspects, the system is configured to extract features from the microphone signals representing speech of the ear-wearable device wearer and transmit the extracted features along with data based on the blood pressure sensor to a separate device for analysis of ear-wearable device wearer emotion.

In a twenty-first aspect, in addition to one or more of the preceding or following aspects, or in the alternative to some aspects, the ear-wearable device includes a hearing aid.

In a twenty-second aspect, in addition to one or more of the preceding or following aspects, or in the alternative to some aspects, a system can further include a second ear-wearable device.

In a twenty-third aspect, in addition to one or more of the preceding or following aspects, or in the alternative to some aspects, the system is configured to evaluate changes in emotional state over time.

In a twenty-fourth aspect, a hearing assistance system is included having an ear-wearable device can include a control circuit, and a microphone in electronic communication with the control circuit, wherein the ear-wearable device is configured to monitor signals from the microphone, analyze the signals in order to identify sound generated by the ear-wearable device wearer, and transmit data based on the signals to a separate device.

In a twenty-fifth aspect, in addition to one or more of the preceding or following aspects, or in the alternative to some aspects, the separate device includes an external accessory device.

In a twenty-sixth aspect, in addition to one or more of the preceding or following aspects, or in the alternative to some aspects, the external accessory device is configured to extract features from the signals representing sound generated by the ear-wearable device wearer and transmit the extracted features to a separate device for analysis of ear-wearable device wearer status.

In a twenty-seventh aspect, in addition to one or more of the preceding or following aspects, or in the alternative to some aspects, the external accessory device is configured to analyze the signals representing sound generated by the ear-wearable device wearer in order to determine ear-wearable device wearer status.

In a twenty-eighth aspect, in addition to one or more of the preceding or following aspects, or in the alternative to some aspects, the ear-wearable device wearer status can include a breathing status.

In a twenty-ninth aspect, in addition to one or more of the preceding or following aspects, or in the alternative to some aspects, the breathing status can include a breathing pattern consistent with sleep apnea, COPD, or another disease state.

In a thirtieth aspect, a method of evaluating the emotional state of an ear-wearable device wearer is included and can include monitoring signals from a microphone forming part of an ear-wearable device, analyzing the microphone signals in order to identify speech, and transmitting data based on the microphone signals representing the identified speech to a separate device.

In a thirty-first aspect, in addition to one or more of the preceding or following aspects, or in the alternative to some aspects, the ear-wearable device is configured to analyze the microphone signals in order to identify speech of the ear-wearable device wearer.

In a thirty-second aspect, in addition to one or more of the preceding or following aspects, or in the alternative to some aspects, the separate device is configured to analyze the microphone signals in order to identify speech of the ear-wearable device wearer.

In a thirty-third aspect, in addition to one or more of the preceding or following aspects, or in the alternative to some aspects, the separate device includes an external accessory device.

In a thirty-fourth aspect, in addition to one or more of the preceding or following aspects, or in the alternative to some aspects, the external accessory device is configured to extract features from the signals representing speech of the ear-wearable device wearer and transmit the extracted features to a separate device for analysis of ear-wearable device wearer emotion.

In a thirty-fifth aspect, in addition to one or more of the preceding or following aspects, or in the alternative to some aspects, the extracted features do not include words.

In a thirty-sixth aspect, in addition to one or more of the preceding or following aspects, or in the alternative to some aspects, the method further can include receiving a signal with the ear-wearable device from the separate device requesting that data based on the microphone signals be sent from the ear-wearable device to the separate device.

In a thirty-seventh aspect, a method of evaluating the emotional state of an ear-wearable device wearer can include receiving a signal with an ear-wearable device from a separate device requesting that an audio recording be sent, monitoring signals from a microphone with the ear-wearable device to detect the device wearer's voice and a volume of background sound below a threshold value, and streaming audio from the ear-wearable device to the separate device reflecting the device wearer's voice.

In a thirty-eighth aspect, in addition to one or more of the preceding or following aspects, or in the alternative to some aspects, a method can further include sending a signal from the separate device to the ear-wearable device requesting an audio recording, receiving the streamed audio with the separate device, extracting features from the streamed audio, and transmitting the extracted features to an emotion analysis system.

In a thirty-ninth aspect, in addition to one or more of the preceding or following aspects, or in the alternative to some aspects, a method further can include receiving emotion information back from the emotion analysis system, and storing the receiving emotion information.

In a fortieth aspect, in addition to one or more of the preceding or following aspects, or in the alternative to some aspects, the separate device sends a signal to the ear-wearable device requesting an audio recording from 10 to 50 times per day.

In a forty-first aspect, in addition to one or more of the preceding or following aspects, or in the alternative to some aspects, a method further can include sending sensor data to the separate device, the sensor data can include at least one of motion sensor data, heart rate sensor data, blood pressure sensor data, temperature sensor data, and geolocation data.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An ear-wearable device comprising:

an ear-wearable device housing configured to be worn within or on an ear of a wearer, the ear-wearable device housing containing:

a control circuit;

a microphone, wherein the microphone is in electrical communication with the control circuit; and a power supply circuit, wherein the power supply circuit is in electrical communication with the control circuit;

a receiver configured to convert electrical impulses into sound, wherein the receiver is in electrical communication with the control circuit;

an antenna arrangement, wherein the antenna arrangement is in electrical communication with the control circuit; and a sensor package, wherein the sensor package is in electrical communication with the control circuit;

wherein the ear-wearable device is configured to:

monitor signals from the microphone;

monitor signals from the sensor package;

analyze the monitored signals from the microphone to identify speech of the wearer;

identify, via the control circuit, signs of anxiety in the identified speech over a particular time frame;

transmit, via the antenna arrangement, data based on the signs of anxiety in the signals representing the identified speech and data based on the signals from the sensor package to a separate device that identifies an underlying emotional status or condition of the wearer based on patterns in the signs of anxiety over the particular time frame and a change in signals from the sensor package during a look-back period before the particular time frame;

and provide, via the receiver, the wearer of the ear-wearable device with auditory feedback related to the identified underlying emotional status or condition.

2. The ear-wearable device of claim 1, wherein the feedback comprises suggested anxiety interventions.

3. The ear-wearable device of claim 2, wherein the anxiety interventions include breathing instructions.

4. The ear-wearable device of claim 1, wherein the auditory feedback indicates that anxiety was identified and provides suggested anxiety interventions.

5. The ear-wearable device of claim 1, wherein the sensor package comprises at least one selected from the group consisting of a motion sensor, a heart rate sensor, a temperature sensor, a respiratory rate sensor, and an SpO2 sensor;

wherein the ear-wearable device is configured to monitor signals from the sensor package to identify signs of anxiety.

6. The ear-wearable device of claim 5, wherein signs of anxiety include a change in microphone signals along with a change in signals from at least one sensor in the sensor package.

7. The ear-wearable device of claim 1, wherein the signs of anxiety include at least one of tonal change, volume change, and change of vocal cadence.

8. The ear-wearable device of claim 1, wherein the particular time frame is daily and the separate device is configured to analyze how the data changes over the particular time frame to assess for emotional status or conditions having a circadian type rhythm.

9. The ear-wearable device of claim 1, wherein the signs of anxiety include a change in the speech of the wearer of the ear-wearable device.

10. The ear-wearable device of claim 1, wherein the ear-wearable device is configured to determine a baseline value of anxiety for a wearer of the ear-wearable device.

11. The ear-wearable device of claim 10, wherein the baseline value accounts for at least one of language and persona of the wearer of the ear-wearable device.

12. The ear-wearable device of claim 1, wherein the underlying emotional status or condition comprises any of a circadian type rhythm condition or seasonal affective disorder.

13. The ear-wearable device of claim 1, wherein the separate device is configured to display the data as a function of the particular time frame.

14. An ear-wearable device system comprising:

an ear-wearable device comprising:

an ear-wearable device housing configured to be worn within or on an ear of a wearer, the ear-wearable device housing containing:

a control circuit;

a microphone, wherein the microphone is in electrical communication with the control circuit;

a sensor package, wherein the sensor package is in electrical communication with the control circuit;

a power supply circuit, wherein the power supply circuit is in electrical communication with the control circuit;

a receiver configured to convert electrical impulses into sound, wherein the receiver is in electrical communication with the control circuit; and an antenna arrangement, wherein the antenna arrangement is in electrical communication with the control circuit;

a separate device;

wherein the ear-wearable device is configured to monitor signals from the microphone;

monitor signals from the sensor package;

analyze the monitored signals from the microphone to identify speech of the wearer;

identify, via the control circuit, signs of anxiety in the identified speech over a particular time frame;

transmit, via the antenna arrangement, data based on the signs of anxiety in the signals representing the identified speech and data based on the signals from the sensor package to the separate device that identifies an underlying emotional status or condition of the wearer based on patterns in the signs of anxiety over the particular time frame and a change in signals from the sensor package during a look-back period before the particular time frame; and provide, via the receiver, the ear-wearable device wearer with auditory feedback related to identified underlying emotional status or condition.

15. The ear-wearable device system of claim 14, wherein the sensor package comprises a blood pressure sensor, wherein the previously detected change in the signals from the sensor package comprises a transient change in blood pressure, wherein the ear-wearable device system is configured to correlate the identified anxiety in the microphone signals to the transient change in blood pressure data.

16. The ear-wearable device system of claim 14, wherein the previously detected change in the signals from the sensor package is between about 10 seconds and 600 seconds before the identified anxiety in the microphone signals.

* * * * *